US008820660B2

(12) United States Patent  (10) Patent No.: US 8,820,660 B2
Ajagbe  (45) Date of Patent: Sep. 2, 2014

(54) AROMATIC SHOWER HEAD DEVICE

(76) Inventor: Adebowale Ajagbe, Detroit, MI (US)

(\*) Notice: Subject to any disclaimer, the term of this patent is extended or adjusted under 35 U.S.C. 154(b) by 301 days.

(21) Appl. No.: 13/228,067

(22) Filed: Sep. 8, 2011

(65) Prior Publication Data

US 2012/0091231 A1  Apr. 19, 2012

Related U.S. Application Data

(60) Provisional application No. 61/394,119, filed on Oct. 18, 2010.

(51) Int. Cl.
- *B05B 7/26* (2006.01)
- *B05B 7/24* (2006.01)
- *B05B 1/18* (2006.01)
- *A61L 9/04* (2006.01)
- *A61L 9/05* (2006.01)
- *E03C 1/046* (2006.01)

(52) U.S. Cl.
CPC ............... *B05B 1/18* (2013.01); *B05B 7/2462* (2013.01); *E03C 1/046* (2013.01); *A61L 9/048* (2013.01); *A61L 9/05* (2013.01); *A61L 2209/133* (2013.01)
USPC .......................................... 239/315; 239/316

(58) Field of Classification Search
CPC .............................. B05B 7/24; B05B 7/2462
USPC ......... 239/315, 310, 316, 302, 344, 354, 409, 239/569
See application file for complete search history.

(56) References Cited

U.S. PATENT DOCUMENTS

| | | | | |
|---|---|---|---|---|
| 4,055,278 A | * | 10/1977 | Seymour | 222/42 |
| 4,211,368 A | | 7/1980 | Legros et al. | |
| 4,623,095 A | | 11/1986 | Pronk | |
| 5,356,076 A | * | 10/1994 | Bishop | 239/311 |
| 5,915,622 A | | 6/1999 | Foote | |
| 6,419,166 B1 | | 7/2002 | Brzezinski et al. | |
| 7,093,775 B1 | | 8/2006 | Bingham | |
| 7,975,936 B2 | | 7/2011 | Paoluccio | |

\* cited by examiner

*Primary Examiner* — Davis Hwu

(74) *Attorney, Agent, or Firm* — Gifford, Krass, Sprinkle, Anderson & Citkowski, P.C.

(57) ABSTRACT

A shower head assembly having a fragrant releasing device operable to release a scent when water is passed through the shower head assembly is provided. Preferably the fragrant releasing device is formed in part by a gelatinous material operable to release a predetermined scent when placed in contact with water. The shower head assembly includes a housing and an outlet. In one embodiment, the shower head assembly includes a spacer disposed in a gap between the face of the outlet and an outer edge of the housing. The fragrant releasing device is disposed within the chamber so as to be in fluid communication with the inner space of the housing. In another embodiment, the chamber is disposed on the face. A cartridge is configured to be fittingly disposed within the chamber. The cartridge releases a scent when water is introduced into the housing and through the nozzles of the face.

6 Claims, 8 Drawing Sheets

AROMATIC SHOWER HEAD DEVICE

CROSS-REFERENCE TO RELATED APPLICATIONS

This Application claims the benefit of U.S. Provisional Application 61/394,119 filed on Oct. 18, 2010, the disclosure of which is incorporated by reference herein in its entirety.

FIELD OF THE INVENTION

The invention relates to a shower head assembly. More particularly, the invention relates to a shower head assembly having a fragrant releasing device operable to release a scent when water is ejected through the shower head assembly.

BACKGROUND OF THE INVENTION

Shower head assemblies are currently known and used. They are often configured with various different nozzles and valves to emit different types of spray. Soaps having various scents are used when showering. Some of the scents have aromatic therapeutic value. For instance, it is often thought that the smell of mint helps clear up the nasal passages. In other instances it is just desirable and more pleasurable to add various smells so that the user feels clean and has a more enjoyable showering experience. However, soap adds additional cost and is labor intensive in terms of application, and thus may add stress to what should otherwise be an enjoyable experience. Accordingly, it remains desirable to have a device which releases aromatic scents for therapeutic value or just to increase the enjoyment of a showering experience without the added cost of soap and the added labor required to rub the soap on one's body.

SUMMARY OF THE INVENTION AND ADVANTAGES

The present invention provides a shower head assembly having a fragrant releasing device operable to release a scent when water is passed through the shower head assembly. Preferably the fragrant releasing device is formed in part by a gelatinous material operable to release a predetermined scent when placed in contact with water. The shower head assembly includes a housing and an outlet. The outlet includes a face having a plurality of nozzles in fluid communication with the inner chamber of the housing.

In a first preferred embodiment, the shower head assembly includes a spacer. The spacer is disposed in a gap between the face of the outlet and an outer edge of the housing. The fragrant releasing device is configured to be fittingly disposed within a chamber disposed within the gap. The chamber is in fluid communication with the inner space of the housing. Thus, the fragrant releasing device releases a scent when water is introduced into the housing and through the nozzles of the face.

In a second preferred embodiment, the chamber is disposed on the face. A cartridge is configured to be fittingly disposed within the chamber. Thus, the cartridge releases a scent when water is introduced into the housing and through the nozzles of the face.

In a third preferred embodiment of a shower head assembly includes a fragrant adapter is mounted within the housing. The fragrant adapter includes an elongated tubular body forming a fluid passageway. The fluid passageway includes a second inlet and a second outlet. The second inlet is located upstream the second outlet. The fragrant adapter includes a first port and a second port located downstream the first port.

The fragrant adapter may further include a cartridge. The cartridge is fixedly formed to a portion of the fluid passageway, between the first and second inlets. The cartridge includes a cartridge housing having a cartridge opening and a cartridge lid adapted to engage the cartridge opening so as to enclose the cartridge housing. The shower head assembly may further include a first gasket adapted to fittingly engage the inner wall surface of the cartridge housing may help prevent fluids from escaping past the cartridge lid. The cartridge is configured to retain a fragrant releasing device.

The fragrant releasing device is formed of a gelatinous material which is water soluble. The fragrant releasing device includes a body adapted to fit within the cartridge housing. The gelatinous material may be operable to release aromatic scents upon either direct or indirect contact with water or hot steam which is generated by the water. The gelatinous material may be chemically constructed to release a desired scent such as mint, strawberries, or the like.

The cartridge housing includes a first cartridge housing opening formed along a side wall and a second cartridge housing opening. The first cartridge housing is in fluid communication with the first port of the fluid passageway. The second cartridge housing opening is in fluid communication with inner spaces of the fluid passageway. As water is introduced into the second inlet, water passes into the cartridge housing via the first port, engages the fragrant releasing device so as to release a fragrance into the environment. Water is then ejected through the second cartridge housing opening and out the nozzles.

The shower head assembly may further include a valve assembly operable to close fluid communication between the port and the cartridge. The valve assembly may include a first cylindrical tube member having a pair of apertures formed along the wall of the first cylindrical tube member. One of the pair of apertures is in fluid communication with the fluid passageway, and the other of the pair of apertures is in fluid communication with the first port.

A cylindrical body member adapted to rotatably fit within the first cylindrical tube member. The cylindrical body member includes a through-bore. Each end of the through-bore may be rotated so to be registered with a respective one of the pair of apertures so as to present a passage for water into the cartridge.

The valve assembly may include a handle operable to rotate the cylindrical body member. Thus, the cylindrical body member may be rotated between an open and a closed position. In the open position, each end of the through-bore is registered with a respective one of the pair of apertures so as to present a passage for water into the cartridge housing. In the closed position, the ends of the through-bore are displaced from each of the pair of apertures so as to block water from entering into the cartridge housing.

The shower head assembly may further include a ball joint assembly for rotatable mounting to the spigot. The ball joint assembly includes a bearing having a joint passage for fluid to flow through. Specifically, fluid from the spigot may flow through the joint passage of the bearing and into the fluid passageway. The ball joint assembly may further include a socket configured to rotatably housing the bearing. The socket is threadedly coupled to the first opening. The ball joint assembly may further include a collar having a threaded inner surface configured to engage the spigot. The second inlet is in fluid communication the first opening of the housing. The second outlet is in fluid communication with the face.

DETAILED DESCRIPTION OF THE INVENTION

Figure 1:
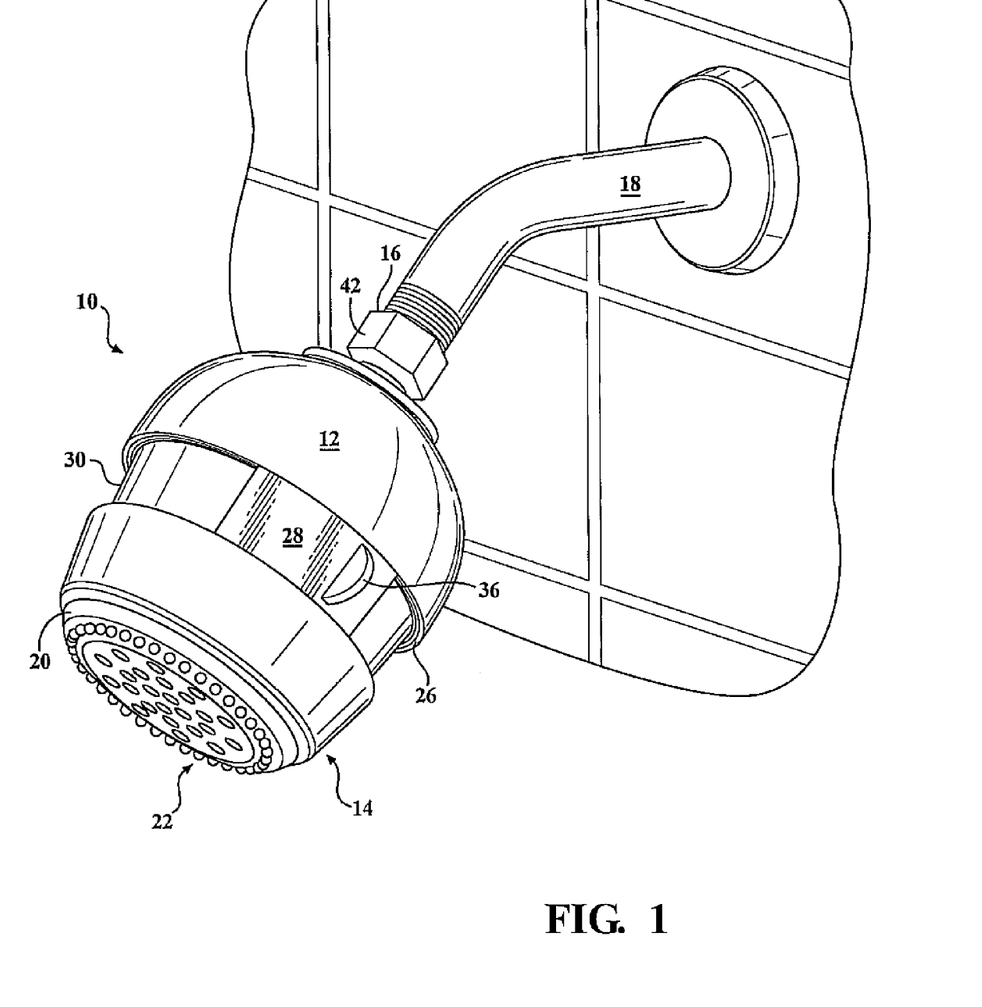
FIG. 1 is a perspective view of a shower head assembly of the first preferred embodiment.
Figure 2:
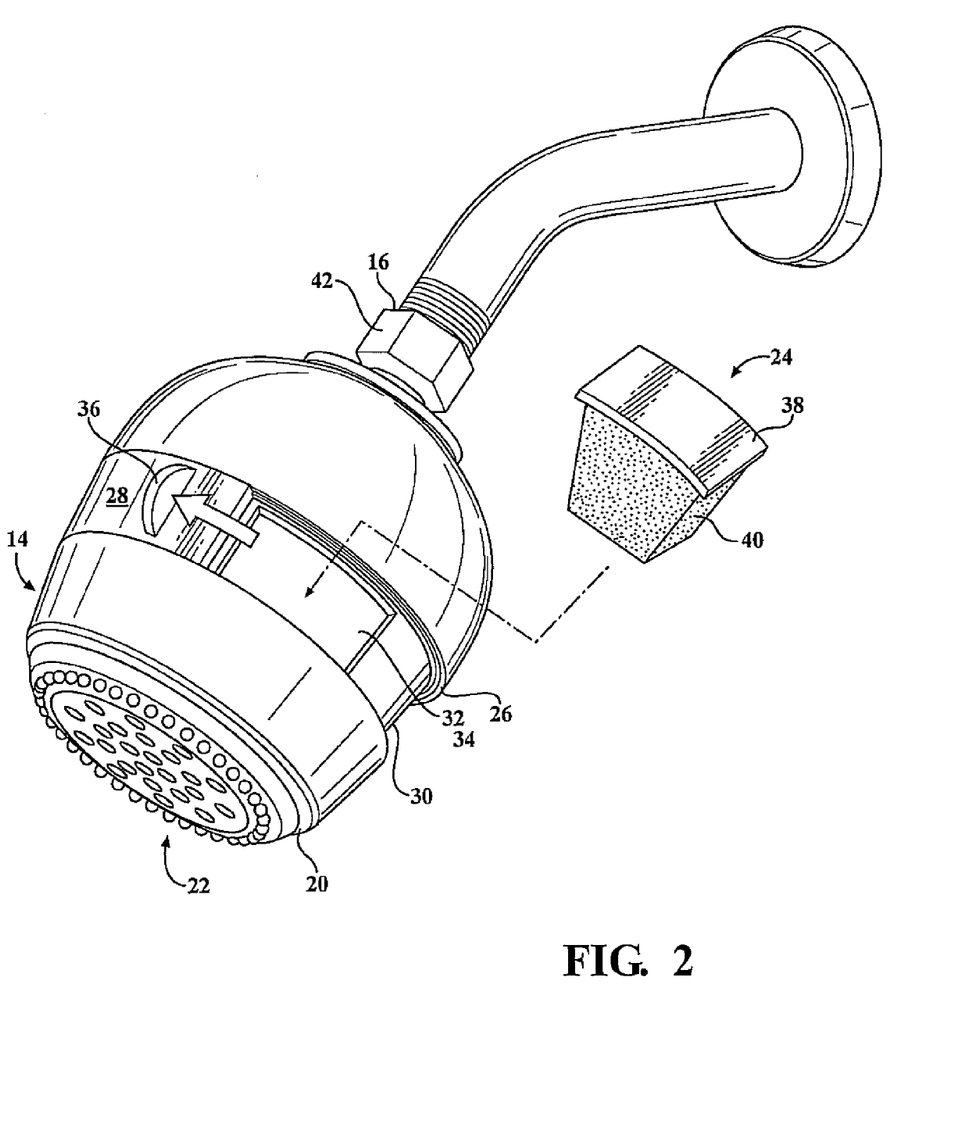
FIG. 2 is an exploded view of the shower head assembly of FIG. 1 showing the fragrant releasing device.

Referring first to FIGS. 1-2, a shower head assembly 10 of the first preferred embodiment is provided. The shower head assembly 10 includes a housing 12 and an outlet 14. The housing 12 encloses an inner space and includes a first opening 16 adapted to engage a spigot 18. The outlet 14 has a face 20 having a plurality of nozzles 22 in fluid communication with the inner space of the housing 12. The nozzles 22 are configured to eject different streams from the outlet 14. The outlet 14 may be rotated so as to actuate or open various nozzles 22 to allow for different stream patterns to be emitted from the shower head assembly 10.

A fragrant releasing device 24 is disposed between a portion of the outlet 14 and the outer edge 26 of the housing 12. The fragrant releasing device 24 is in fluid communication with the inner space of the housing 12 and is operable to release a fragrant when placed in contact with water.

Specifically, the shower head assembly 10 includes a spacer 28 disposed between the face 20 and the outer edge 26 of the housing 12. The face 20 of the outlet 14 is spaced apart from an outer edge 26 of the housing 12 so as to define a gap 30 between the outlet 14 and the outer edge 26 of the housing 12. The spacer 28 may be slid along the gap 30. A chamber 32 having a chamber 32 opening 34 is disposed within the gap 30. The chamber 32 is in fluid communication with the inner space of the housing 12. The spacer 28 may be slid so as to close and expose the chamber 32 opening 34. Specifically, the spacer 28 is movable between a first position wherein the spacer 28 covers the chamber 32 and a second position where the spacer 28 is displaced from the chamber 32. The spacer 28 may further include a tab 36 disposed on the outer surface. As shown in FIG. 2, the tab 36 facilitates the movement of the spacer 28 along the gap 30.

With reference now to FIG. 2, a fragrant releasing device 24 is provided. In a first preferred embodiment, the fragrant releasing device 24 is formed of a gelatinous material which is water soluble. The fragrant releasing device 24 includes a body adapted to fit within the chamber 32. The gelatinous material may be operable to release aromatic scents upon either direct or indirect contact with water or hot steam which is generated by the water. The gelatinous material may be chemically constructed to release a desired scent such as mint, strawberries, or the like.

The fragrant releasing device 24 is configured to be disposed fittingly within the chamber 32. The spacer 28 is configured to be fittingly disposed within the gap 30 so as to prevent water from escaping along the gap 30 and to direct water towards the nozzles 22 which are in communication with the face 20 of the outlet 14. The fragrant releasing device 24 may be formed of two parts 38, 40, the first part 38 being a rigid plastic or rubber which is resistant to erosion and water damage.

The first part 38 forms an outer surface of the fragrant releasing device 24 and may fit within the chamber 32 opening 34 so as to form a seal to help prevent water from escaping. The second part 40 forms the inner portion of the fragrant releasing device 24. The second part 40 may be formed of a gelatinous material that is chemically formed so as to slowly degrade and release aromatic scents over a period of time.

In operation, the user may push the spacer 28 to the open position and insert a fragrant releasing device 24 into the chamber 32 such that the first part 38 is engaged within the chamber 32 opening 34. The spacer 28 is then moved to the closed position. The user then turns on the spigot 18 and a fragrance is released when water comes into contact with the gelatinous material disposed within the inner space of the housing 12.

The housing 12 may be formed of a rigid material such as plastic or metal. The inner surface of the housing 12 defines a passage for fluids to pass. The housing 12 includes an adaptor 42 disposed opposite the outlet 14. The adaptor 42 is operable to be threadedly coupled with a spigot 18. The outlet 14 is configured to form channels for which water may flow from the adaptor 42 and to respective nozzles 22 on the face 20. Shower heads 44 are currently known and used in the art and any such shower head 44 may be adaptable for use herein.

Figure 3:
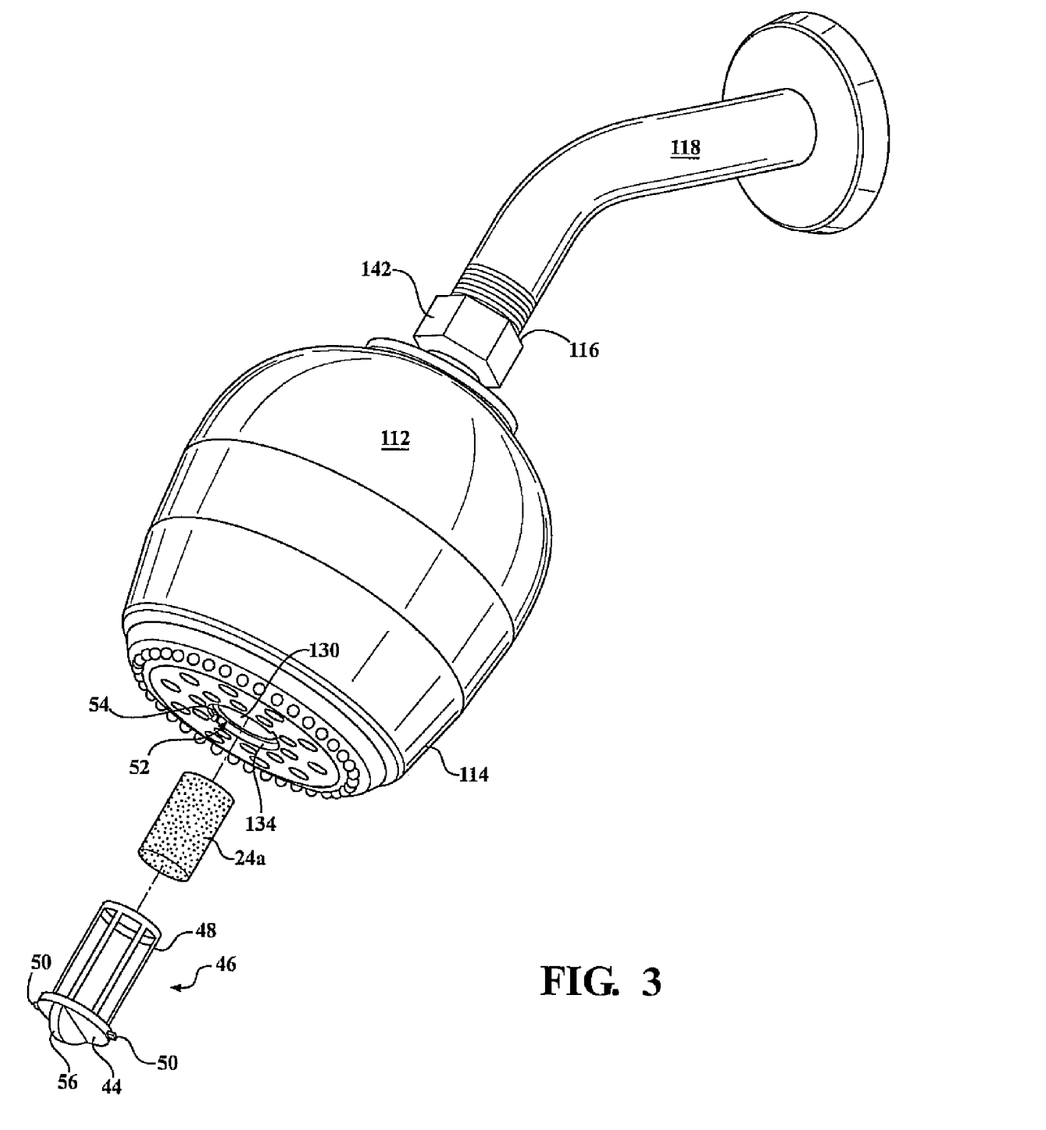
FIG. 3 is a perspective view a second preferred embodiment of the shower head.
Figure 4:
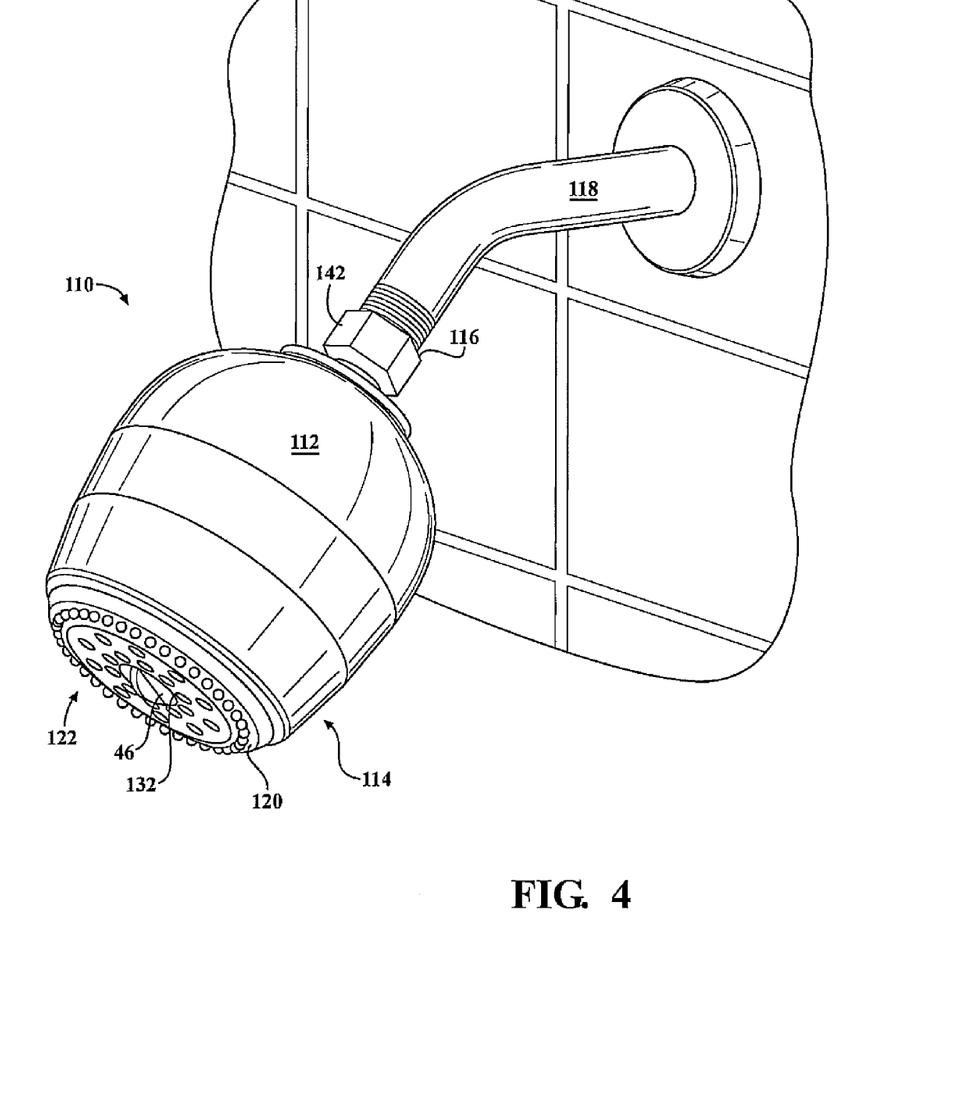
FIG. 4 is an exploded view of the shower head assembly of FIG. 3 showing the fragrant releasing device.

With reference now to FIGS. 3 and 4, a second preferred embodiment of a shower head assembly 10 of the present invention is provided, wherein like parts 38, 40 are indicated by numerals offset by 100. The chamber 32 is disposed on the face 20 of the shower head assembly 10. The chamber 32 includes a chamber 32 opening 34 that is generally disposed in the center of the face 20. The fragrant releasing device 24 is a cartridge 46 configured to fittingly engage the chamber 32 opening 34 of the chamber 32.

The cartridge 46 includes a head 44 and a retainer 48 adapted to hold a gelatinous material 24a operable to release a chemically manufactured scent when placed in contact with water. The head 44 may include a pair of male members 50 disposed on the outer side surfaces of the head 44. The chamber 32 opening 34 of the face 20 may include a pair of slots 52 adapted to receive the respective male members 50 of the head 44. The slots 52 may extend radially so as to form channels adapted to fit the male members 50. The channels allow the head 44 to be rotated and the male members 50 to be seated within the face 20. The head 44 may include a handle 54 so as to facilitate insertion of the cartridge 46 into the face 20 of the shower head assembly 10.

Thus, in operation, the user inserts the cartridge 46 into the face 20 by aligning the male members 50 of the head 44 with the slots 52 of the chamber 32 opening 34. The head 44 is then rotated so as to slide the male members 50 into respective channels and lock the cartridge 46 into place with the head 44. The retainer 48 of the cartridge 46 is then disposed within the inner chamber 32 of the housing 12. Thus as a user turns on the water, water is ejected from the spigot 18 and through the adaptor 42 into the chamber 32 defined by the inner surface wall of the housing 12. As water comes into contact with the gelatinous material disposed, an aroma is dispensed as the water is dispensed through the nozzles 22. It should be appreciated that the fragrant releasing device 24 may be configured to last for a predetermined period of time, and come in different scents.

When all of the gelatinous material is dissolved, the user may simply insert a new cartridge 46 into the face 20 of the shower head assembly 10 by simply rotating the cartridge 46 in the opposite direction until the male members 50 are aligned with the slots 52. The cartridge 46 may then be replaced.

Figures 5, 8:
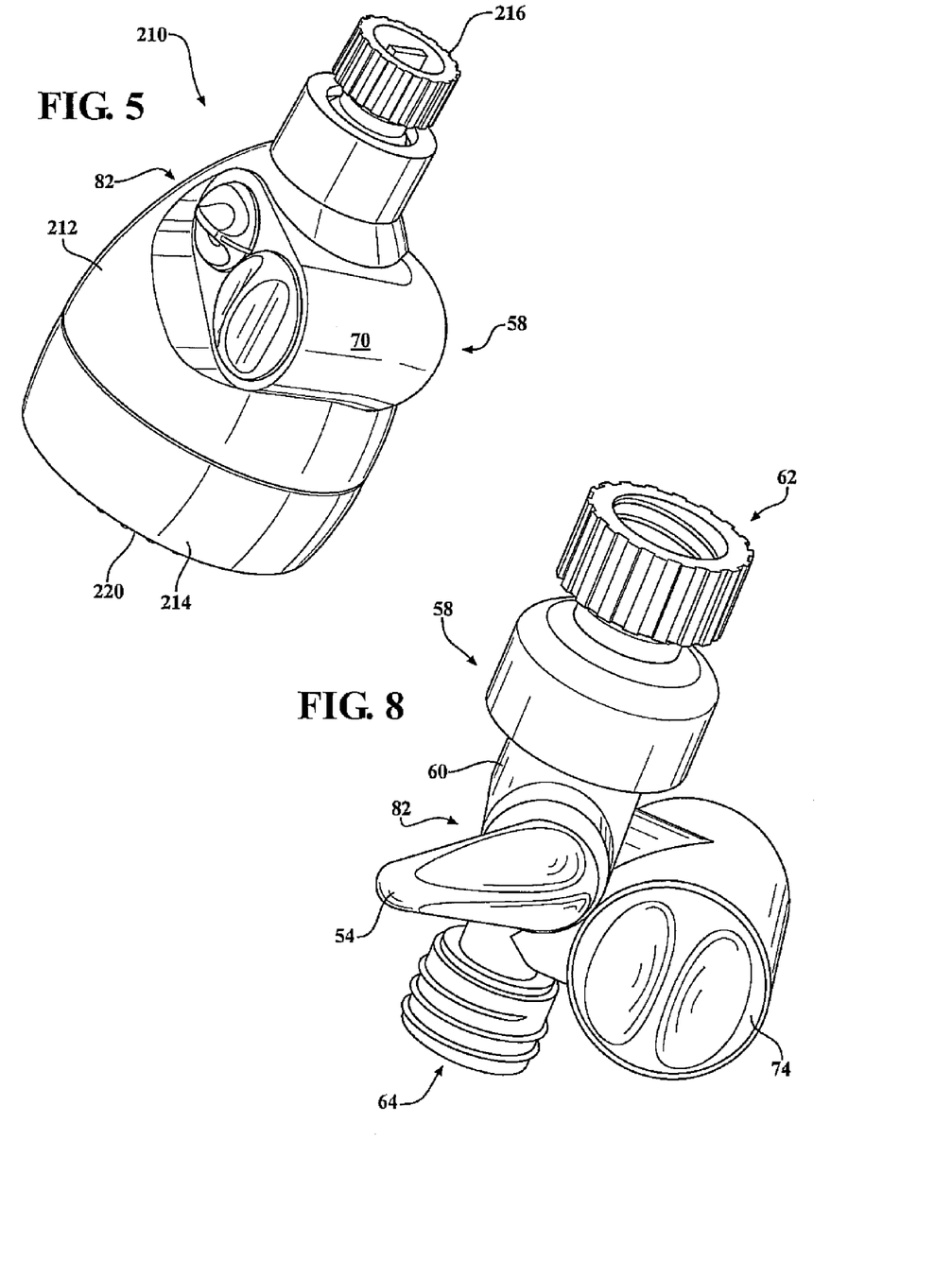
FIG. 5 is a perspective view of a shower head assembly of a third preferred embodiment.
FIG. 8 is a perspective view of a fragrant adapter.
Figure 6:
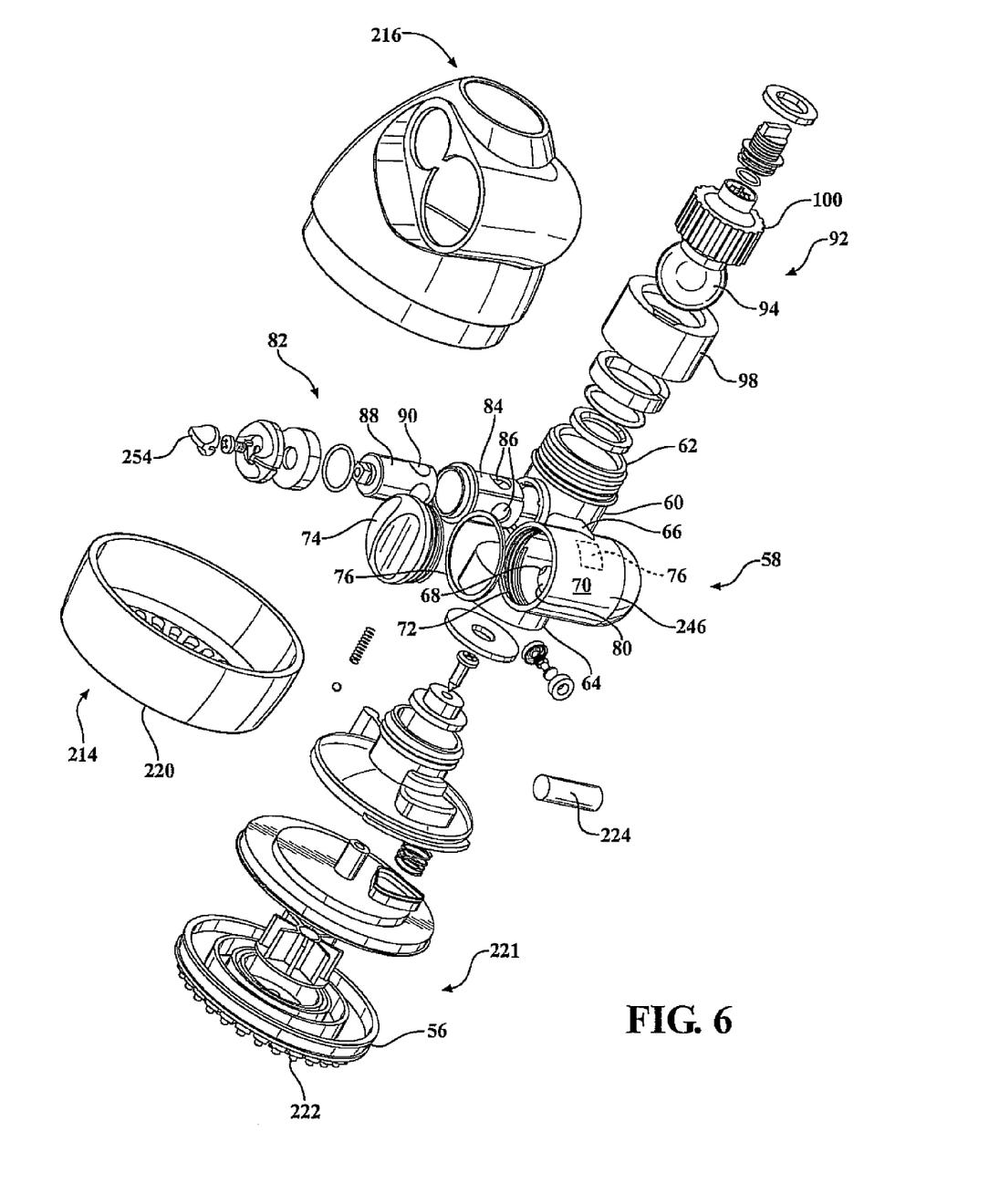
FIG. 6 is an exploded view of the shower head assembly of FIG. 5.
Figure 7:
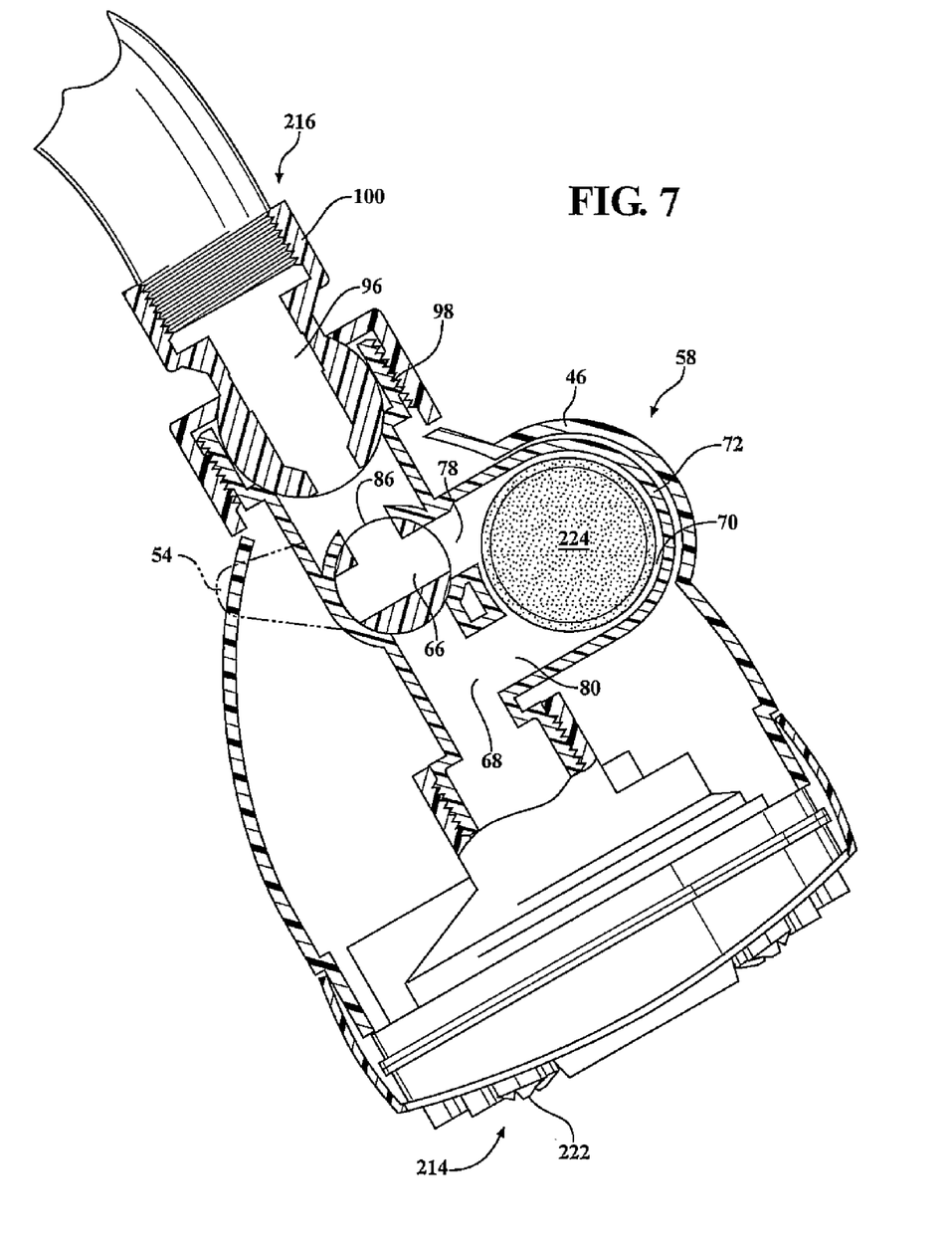
FIG. 7 is a cross-sectional view of the shower head assembly of FIG. 5.

With reference now to FIGS. 5-7, a third preferred embodiment of a shower head assembly 10 of the present invention is provided, wherein like parts are indicated by numerals offset by 200. The shower head assembly 210 includes a housing 212 and an outlet 214. The housing 212 encloses an inner space and includes a first opening 216 adapted to engage a spigot 218. The outlet 214 has a face 220 and a nozzle 222 assembly, generally indicated by reference numeral 221. The nozzle assembly includes a first plate 56 having a plurality of nozzles 222 in fluid communication with the inner space of the housing 212. The nozzles 222 are configured to eject different streams from the outlet 214. The outlet 214 may be rotated so as to actuate or open various nozzles 222 to allow for different stream patterns to be emitted from the shower head assembly 210.

A fragrant adapter 58 is mounted within the housing 212. The fragrant adapter 58 includes an elongated tubular body forming a fluid passageway 60. The fluid passageway 60 includes a second inlet 62 and a second outlet 64. The second inlet 62 is located upstream the second outlet 64. The fragrant adapter 58 includes a first port 66 and a second port 68 located downstream the first port 66.

The fragrant adapter 58 may further include a cartridge 246. The cartridge 246 is fixedly formed to a portion of the fluid passageway 60, between the second inlet 62 and the second outlet 64. The cartridge 246 includes a cartridge housing 70 having a cartridge opening 72 and a cartridge lid 74 adapted to engage the cartridge opening 72 so as to enclose the cartridge housing 70. The shower head assembly 210 may further include a first gasket 76 adapted to fittingly engage the inner wall surface of the cartridge housing 70 may help prevent fluids from escaping past the cartridge lid 74. The cartridge 246 is configured to retain a fragrant releasing device 224.

The fragrant releasing device 224 is formed of a gelatinous material which is water soluble. The fragrant releasing device 224 includes a body adapted to fit within the cartridge housing 70. The gelatinous material may be operable to release aromatic scents upon either direct or indirect contact with water or hot steam which is generated by the water. The gelatinous material may be chemically constructed to release a desired scent such as mint, strawberries, or the like.

The cartridge housing 70 includes a first cartridge housing opening 78 formed along a side wall and a second cartridge housing opening 80. The first cartridge housing 70 is in fluid communication with the first port 66 of the fluid passageway 60. The second cartridge housing opening 80 is in fluid communication with inner spaces of the fluid passageway 60. As water is introduced into the second inlet 62, water passes into the cartridge housing 70 via the first port 66, engages the fragrant releasing device 224 so as to release a fragrance into the environment. Water is then ejected through the second cartridge housing opening 80 and out the nozzles 22.

The shower head assembly 210 may further include a valve assembly 82 operable to close fluid communication between the first port 66 and the cartridge 246. The valve assembly 82 may include a first cylindrical tube member 84 having a pair of apertures 86 formed along the wall of the first cylindrical tube member 84. One of the pair of apertures 86 is in fluid communication with the fluid passageway 60, and the other of the pair of apertures 86 is in fluid communication with the first port 66.

A cylindrical body member 88 adapted to rotatably fit within the first cylindrical tube member 84. The cylindrical body member 88 includes a through-bore 90. Each end of the through-bore 90 may be rotated so to be registered with a respective one of the pair of apertures 86 so as to present a passage for water into the cartridge 246.

The valve assembly 82 may include a handle 254 operable to rotate the cylindrical body member 88. Thus, the cylindrical body member 88 may be rotated between an open and a closed position. In the open position, each end of the through-bore 90 is registered with a respective one of the pair of apertures 86 so as to present a passage for water into the cartridge housing 70. In the closed position, the ends of the through-bore 90 are displaced from each of the pair of apertures 86 so as to block water from entering into the cartridge housing 70.

The shower head assembly 210 may further include a ball joint assembly 92 for rotatable mounting to the spigot 18. The ball joint assembly 92 includes a bearing 94 having a joint passage 96 for fluid to flow through. Specifically, fluid from the spigot 218 may flow through the joint passage 96 of the bearing 94 and into the fluid passageway 60. The ball joint assembly 92 may further include a socket 98 configured to rotatably housing 12 the bearing 94. The socket 98 is threadedly coupled to the second inlet 62. The ball joint assembly 92 may further include a collar 100 having a threaded inner surface configured to engage the spigot 218. The second inlet 62 is in fluid communication the first opening 216 of the housing 212. The second outlet 64 in fluid communication with the face 220.

Figure 9:
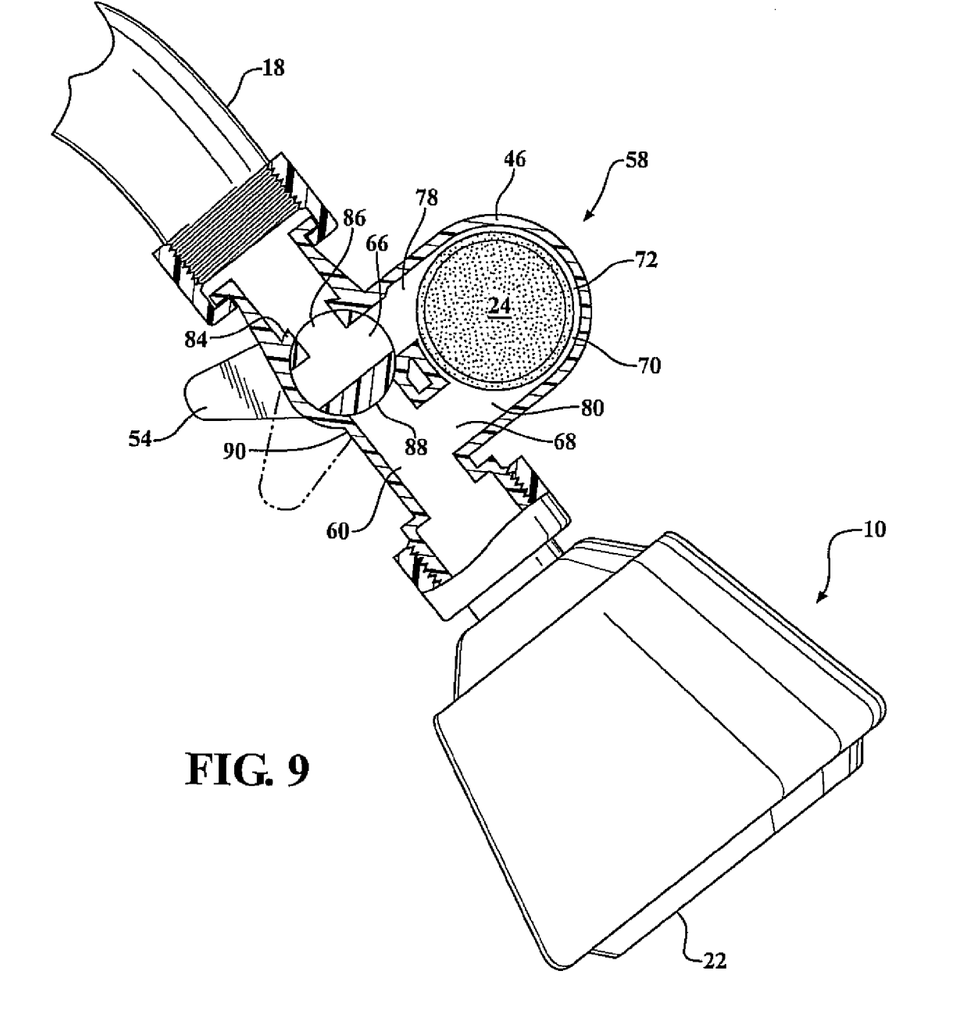
FIG. 9 is a cross-sectional view of the fragrant adapter of FIG. 7 mounted between a spigot and shower head assembly of the prior art.

With reference now to FIGS. 8 and 9, an illustration of a fragrant adapter 58 for use with a shower head assembly 10 is provided. The fragrant adapter 58 includes an elongated tubular body forming a fluid passageway 60. The fluid passageway 60 includes a second inlet 62 and a second outlet 64. The second inlet 62 is located upstream the second outlet 64. The second inlet 62 is configured to mount onto a spigot 18. The second outlet 64 is configured to mount onto the inlet end of a shower head assembly 10.

The fragrant adapter 58 includes a first port 66 and a second port 68 located downstream the first port 66. The fragrant adapter 58 may further include a cartridge 46. The cartridge 46 is fixedly formed to a portion of the fluid passageway 60, between the first and second inlets 62. The cartridge 46 includes a cartridge housing 70 having a cartridge opening 72 and a cartridge lid 74 adapted to engage the cartridge opening 72 so as to enclose the cartridge housing 70.

The cartridge 46 is configured to retain a fragrant releasing device 24. The fragrant releasing device 24 is formed of a gelatinous material which is water soluble. The fragrant releasing device 24 includes a body adapted to fit within the cartridge housing 70. The gelatinous material may be operable to release aromatic scents upon either direct or indirect contact with water or hot steam which is generated by the water. The gelatinous material may be chemically constructed to release a desired scent such as mint, strawberries, or the like.

The cartridge housing 70 includes a first cartridge housing opening 78 formed along a side wall and a second cartridge housing opening 80. The first cartridge housing 70 is in fluid communication with the first port 66 of the fluid passageway 60. The second cartridge housing opening 80 is in fluid communication with second port 68 of the fluid passageway 60. As water is introduced into the second inlet 62, water passes into the cartridge housing 70 via the first port 66, engages the fragrant releasing device 24 so as to release a fragrance into the environment. Water is then ejected through the second cartridge housing opening 80 and out the nozzles 22.

The fragrant adapter 58 may further include a valve assembly 82 operable to close fluid communication between the port and the cartridge 46. The valve assembly 82 may include a first cylindrical tube member 84 having a pair of apertures 86 formed along the wall of the first cylindrical tube member 84. One of the pair of apertures 86 is in fluid communication with the fluid passageway 60, and the other of the pair of apertures 86 is in fluid communication with the first port 66.

A cylindrical body member 88 adapted to rotatably fit within the first cylindrical tube member 84. The cylindrical body member 88 includes a through-bore 90. Each end of the through-bore 90 may be rotated so to be registered with a respective one of the pair of apertures 86 so as to present a passage for water into the cartridge 46.

The valve assembly 82 may include a handle 54 operable to rotate the cylindrical body member 88. Thus, the cylindrical body member 88 may be rotated between an open and a closed position. In the open position, each end of the through-bore 90 is registered with a respective one of the pair of apertures 86 so as to present a passage for water into the cartridge housing 70. In the closed position, the ends of the through-bore 90 are displaced from each of the pair of apertures 86 so as to block water from entering into the cartridge housing 70.

The fragrant adapter 58 may further include a ball joint assembly 92 for rotatable mounting to the spigot 18. The ball joint assembly 92 includes a bearing 94 having a joint passage 96 for fluid to flow through. Specifically, fluid from the spigot 18 may flow through the bearing 94 and into the fluid passageway 60. The ball joint assembly 92 may further include a socket 98 configured to rotatably housing 12 the bearing 94. The socket 98 is threadedly coupled to the first opening 216, and a collar 100 having a threaded inner surface configured to engage the spigot 18, the second inlet 62 in fluid communication the first opening 16 of the housing 12, the second outlet 64 in fluid communication with the face 20

The invention has been described in an illustrative manner. It is therefore to be understood that the terminology used is intended to be in the nature of words of description rather than limitation. Many modifications and variations of the invention are possible in light of the above teachings. For example, the shower face 20 and the outlet 14 may further include a plurality of valves operable to open and close respective nozzles 22 depending on the rotation of the shower face 20 with respect to the outlet 14.

What is claimed is:

1. A shower head assembly mounted to a spigot for dispensing water, the shower head assembly operable to dispense a fragrance released by a fragrance releasing device, the shower head assembly comprising:

a showerhead enclosing an inner space in communication with a first opening adaptable to engage the spigot;

a face having a plurality of nozzles each in fluid communication with the inner space of the showerhead;

a fragrant adapter having a fluid passageway and a cartridge, the cartridge fully encapsulated within inner space of the showerhead, the fluid passageway having a second inlet and a second outlet, the second inlet in fluid communication the first opening of the showerhead, the second outlet in fluid communication with the face, the fluid passageway including a port in fluid communication with the cartridge; and a ball joint mounted to the first opening, the ball joint including a bearing having a joint passage for fluid to flow through, a socket configured to rotatably house the bearing, and a collar having a threaded inner surface configured to engage the spigot, the cartridge configured to contain the fragrant releasing device when the joint passage is placed in fluid communication with the fluid passageway.

2. The shower head assembly as set forth in claim 1, wherein the cartridge includes a cartridge housing having a cartridge opening and a cartridge lid adapted to engage the opening so as to enclose the cartridge housing.

3. The shower head assembly as set forth in claim 1, further including a valve assembly operable to close fluid communication between the port and the cartridge.

4. A fragrant adapter for use with a shower head assembly, the shower head assembly having a first opening configured to threadedly engage a spigot, a showerhead enclosing an inner space, the fragrant adapter comprising:

a fluid passageway and a cartridge configured to be fully encapsulated within inner space of the showerhead, the fluid passageway having a second inlet and a second outlet, the second inlet in fluid communication the first opening of the showerhead, the second outlet in fluid communication with the first opening of the shower head assembly, the fluid passageway including a port in fluid communication with the cartridge, the cartridge configured to contain the fragrant releasing device; and a ball joint mounted to the first opening, the ball joint including a bearing having a joint passage for fluid to flow through, a socket configured to rotatably house the bearing, and a collar having a threaded inner surface configured to engage the spigot, the fragrant adapter operable release a fragrance when the joint passage is placed in fluid communication with the fluid passageway.

5. The fragrant adapter as set forth in claim 4, wherein the cartridge includes a cartridge housing having a cartridge opening and a cartridge lid adapted to engage the opening so as to enclose the cartridge housing.

6. The fragrant adapter as set forth in claim 4, further including a valve assembly operable to close fluid communication between the port and the cartridge.

* * * * *

UNITED STATES PATENT AND TRADEMARK OFFICE
CERTIFICATE OF CORRECTION

PATENT NO.           : 8,820,660 B2                                Page 1 of 1
APPLICATION NO.      : 13/228067
DATED                : September 2, 2014
INVENTOR(S)          : Adebowale Ajagbe It is certified that error appears in the above-identified patent and that said Letters Patent is hereby corrected as shown below:

In the Claims

At column 8, claim number 1, line number 6, After within, Insert --the--

At column 8, claim number 1, line number 9, After communication, Insert --with--

At column 8, claim number 4, line number 36, After communication, Insert --with--

At column 8, claim number 4, line number 47, After operable, Insert --to--

Signed and Sealed this
Twenty-first Day of July, 2015

Michelle K. Lee
*Director of the United States Patent and Trademark Office*